US008374925B2

(12) United States Patent
Liamos et al.

(10) Patent No.: US 8,374,925 B2
(45) Date of Patent: Feb. 12, 2013

(54) METHOD AND SYSTEM FOR MONITORING CONSUMABLE ITEM USAGE AND PROVIDING REPLENISHMENT THEREOF

(75) Inventors: Charles T. Liamos, Pleasanton, CA (US); Lawrence W. Huffman, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 463 days.

(21) Appl. No.: 12/393,891

(22) Filed: Feb. 26, 2009

(65) Prior Publication Data

US 2009/0326829 A1 Dec. 31, 2009

Related U.S. Application Data

(63) Continuation-in-part of application No. 11/118,796, filed on Apr. 29, 2005.

(51) Int. Cl.
*G06Q 10/00* (2012.01)
(52) U.S. Cl. ......................... 705/28; 705/26.2
(58) Field of Classification Search .................. 600/300, 600/365; 604/66; 705/2, 3, 7, 28
See application file for complete search history.

(56) References Cited

U.S. PATENT DOCUMENTS

| 5,897,622 | A | 4/1999 | Blinn et al. |
|---|---|---|---|
| 5,905,973 | A | 5/1999 | Yonezawa et al. |
| 5,909,023 | A | 6/1999 | Ono et al. |
| 5,937,391 | A | 8/1999 | Ikeda et al. |
| 5,970,462 | A | 10/1999 | Reichert |
| 6,204,763 | B1 | 3/2001 | Sone |
| 6,249,773 | B1 | 6/2001 | Allard et al. |
| 6,336,100 | B1 | 1/2002 | Yamada |
| 6,539,281 | B2 | 3/2003 | Wan et al. |
| 6,729,360 | B2 | 5/2004 | Sesek et al. |
| 6,963,851 | B1 | 11/2005 | Szabo et al. |
| 6,965,871 | B1 | 11/2005 | Szabo et al. |
| 6,973,943 | B2 | 12/2005 | Sesek et al. |
| 7,013,125 | B2 | 3/2006 | Henrikson et al. |
| 7,031,693 | B2 | 4/2006 | Öhrström et al. |
| 7,073,710 | B2 | 7/2006 | Chu |
| 7,110,954 | B2 | 9/2006 | Yung et al. |
| 7,130,814 | B1 | 10/2006 | Szabo et al. |
| 7,215,942 | B1 | 5/2007 | McQuaide et al. |
| 7,246,069 | B1 | 7/2007 | O'Hanlon et al. |

(Continued)

OTHER PUBLICATIONS

Tamada, Janet A., et al. "Noninvasive Glucose Monitoring: Comprehensive Clinical Results." JAMA 282.19 (1999): 1839-44. Hoover's Company Profiles; ProQuest Central. Web. Oct. 6, 2012 (Attached).*

(Continued)

*Primary Examiner* — Matthew Gart
*Assistant Examiner* — Rokib Masud
(74) *Attorney, Agent, or Firm* — Edward J. Baba; Marcus T. Hunt; Bozicevic, Field & Francis LLP

(57) ABSTRACT

Method and system for providing a subscription based replenishment transaction of consumable items such as glucose test strips, lancets, and medication, such as insulin, including a data network, a user terminal operatively coupled to the data network, the user terminal configured to receive and transmit data over the data network, and a server terminal operatively coupled to the data network, the server terminal configured to receive from the user terminal a request for establishing an account associated with a consumable item, receive from the user terminal one or more predetermined parameters associated with the account, and generate the account based on the one or more predetermined parameters, where the one or more predetermined parameters include a user specified consumable replenishment level received from the user terminal is disclosed.

43 Claims, 6 Drawing Sheets

U.S. PATENT DOCUMENTS

| | | | |
|---|---|---|---|
| 7,337,129 B1 * | 2/2008 | Lowry et al. | 705/2 |
| 2001/0051893 A1 | 12/2001 | Hanai et al. | |
| 2002/0049638 A1 | 4/2002 | Ito | |
| 2002/0052760 A1 * | 5/2002 | Munoz et al. | 705/2 |
| 2003/0100821 A1 * | 5/2003 | Heller et al. | 600/347 |
| 2003/0229517 A1 * | 12/2003 | Meserol et al. | 705/2 |
| 2004/0015132 A1 * | 1/2004 | Brown | 604/131 |
| 2004/0054263 A1 | 3/2004 | Moerman et al. | |
| 2004/0167464 A1 * | 8/2004 | Ireland et al. | 604/66 |
| 2006/0085281 A1 | 4/2006 | Hanai et al. | |
| 2006/0085282 A1 | 4/2006 | Hanai et al. | |

OTHER PUBLICATIONS

International Search Report and Written Opinion of the International Searching Authority for PCT Application No. PCT/US2006/016385 filed Apr. 26, 2006 to Abbott Diabetes Care Inc. mailed Apr. 15, 2008.

* cited by examiner

METHOD AND SYSTEM FOR MONITORING
CONSUMABLE ITEM USAGE AND
PROVIDING REPLENISHMENT THEREOF

CROSS-REFERENCE

This application is a continuation-in-part application of Ser. No. 11/118,796, filed Apr. 29, 2005, which is incorporated herein by reference in its entirety noting that the current application controls to the extent there is any contradiction with an earlier application and to which application we claim priority under 35 USC §120.

FIELD OF THE INVENTION

The present invention relates to method and system for monitoring and replenishing consumable supply for health testing or monitoring devices using the consumables. More specifically, the present invention relates to the internet or data network enabled system and method for providing a dynamic monitoring and replenishing approach of consumables such as glucose test strips, lancets, and medication, such as insulin, based on the patient's usage and desired predetermined account profile.

BACKGROUND OF THE INVENTION

Patients who rely on the usage of health related testing or monitoring systems typically rely also on a supply of consumables that the health related monitors employ. For example, diabetics that frequently test glucose level using glucose meters such as Freestyle™ or Flash™, also need a supply of single use strips for testing purposes. Indeed, typically, the testing or monitoring devices such as the glucose meters are designed to last a long time which the devices themselves are configured to use consumables such as glucose test strips in order to operate the testing or monitoring devices.

For patients who are frequent users of the testing or monitoring devices, such as diabetics that test several times daily, having an ample supply of the test strips is critical. More often than not, it is the case that patients run out of the test strips which necessitates a trip to the drugstore, which in some cases, may not be practical. Furthermore, it is also inconvenient to consistently maintain a log or keep track of the number of test strips that remain until a new set of strips are purchased. On the other hand, it is wasteful to simply purchase a large quantity of test strips for storage, which may eventually be lost, that take up storage space, and cost a lot of money up front. This is also true for many other medical testing or monitoring devices, including, for example, measurement of blood coagulation times, cholesterol and lipids, and other diagnostic monitoring tests.

Therefore, it would be desirable to have a subscription based type replenishment system for consumables related to testing or monitoring devices such as glucose meters which allows the user to conveniently and easily check for or be notified in advance of a low threshold supply level, and to have the desired amount of consumables placed in order for receipt. Additionally, it would be desirable to have a tracking system that would maintain a current usage level of the consumables and to notify the user of the testing or monitoring device when the supply level of the consumable falls below a predetermined level. Moreover, it would be desirable to integrate such tracking system systems that track user demand to, for example, forecast and anticipate demand, and also to track overall consumption patterns, preference, seasonal demand, geographic demand, and other similar demographic data for use in better managing supply side activities.

SUMMARY OF THE INVENTION

In view of the foregoing, there is provided a system and method for monitoring patient usage of consumables such as glucose test strips, lancets, and medication including, for example, insulin, in conjunction with a health related testing or monitoring device such as glucose meters, or, for example, Prothrombin Time testing, Lipids testing, and other such frequent health related testing or monitoring that uses a disposable component and replenishing the consumables based on patient's profile including patient's predetermined desired replenishment related settings including minimum desired quantity of the disposable component, seasonality or periodicity of demand, the patient's current usage level of the consumables, and the financial account associated with the patient's account for performing purchase transactions.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Before the present embodiments are described, it is to be understood that this invention is not limited to particular embodiment described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
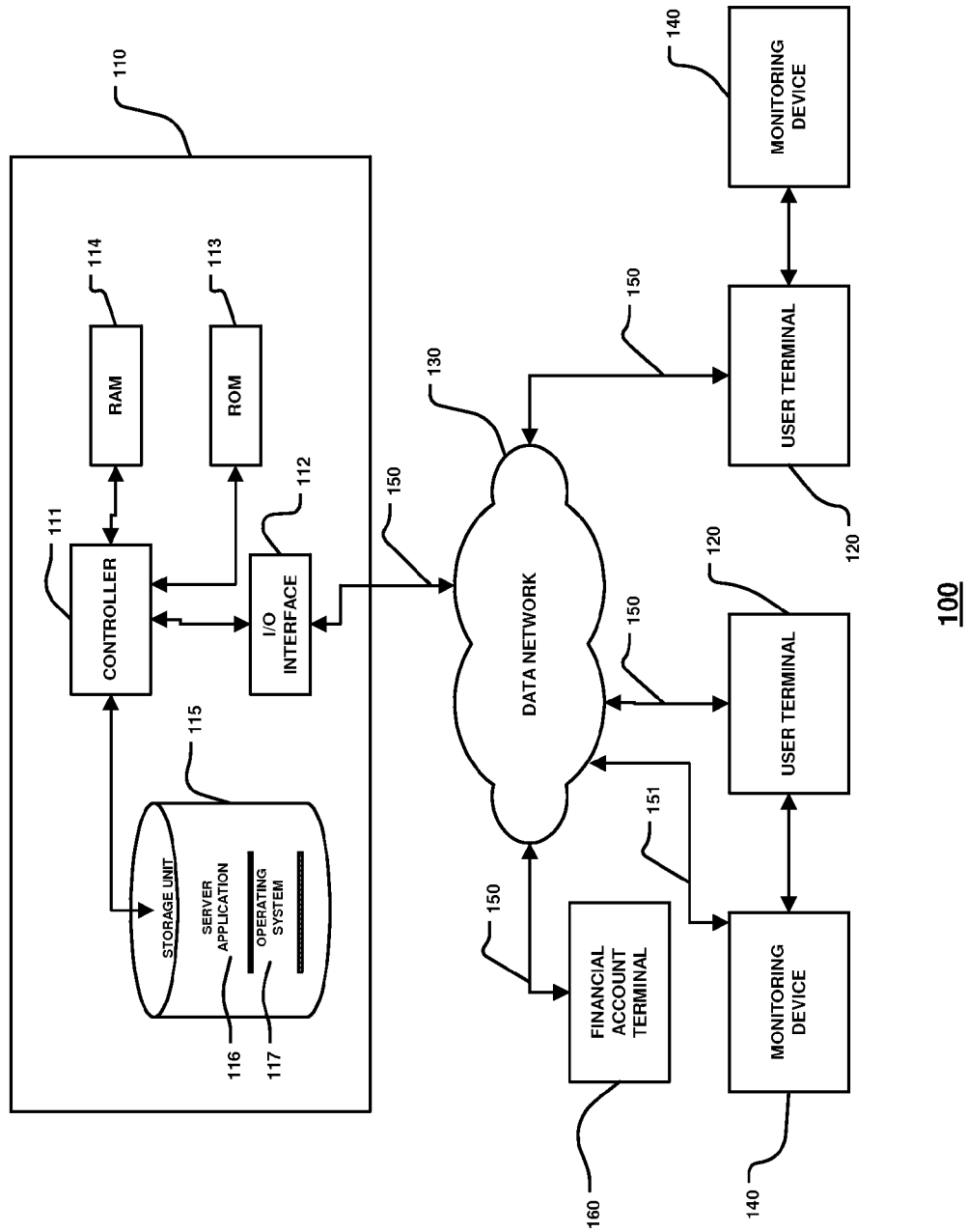
FIG. 1 illustrates a block diagram of a replenishment management system in accordance with one embodiment of the present invention.

FIG. 1 illustrates a block diagram of a replenishment management system in accordance with one embodiment of the present invention. Referring to FIG. 1, the replenishment management system 100 includes a server terminal 110 operatively coupled to one or more user terminals 120 via a data network 130. As can be seen from the Figure, each of the user terminals 12 are also configured to be operatively connected to a respective one or more testing or monitoring devices 140. As will be discussed in further detail below, there is also provided a financial account terminal 160 operatively coupled to the data network 130 for communication with the server terminal 110 and a corresponding one of the user terminals 120.

In one embodiment, the testing or monitoring device 140 may include a glucose meter (for example, glucose meters with wireless communication capabilities) which is configured to automatically and wirelessly transmit the measured glucose data to the server terminal 110 at a predetermined frequency over the wireless connection 151. In this case, the server terminal 110 may be configured to detect and receive the measured glucose data from the glucose meter and to store the received data in a corresponding user account associated with the glucose meter.

In another embodiment, the testing or monitoring device 140 may further include a medication dose calculation function. In such an embodiment, the testing or monitoring device with a medication dose calculation function may include a blood glucose meter with bolus calculation function configured to calculate a single dose bolus dosage of a medication such as insulin such as long acting, fast acting or rapid acting insulin. The test strip for use in conjunction with the health monitor device with a medication dose calculation function, may be a blood glucose test strip configured to receive a blood sample thereon, in order to determine a blood glucose level of the received blood sample.

In accordance with the various embodiments of the present disclosure, the testing or monitoring device 140 with a medication dose calculation function may be configured to automatically enter into a medication dosage calculation mode to, for example, estimate the a medication dosage amount based on information stored in the testing or monitoring device with a medication dose calculation function (such as the patient's insulin sensitivity, for example), and/or prompt the patient to provide additional information, such as the amount of carbohydrate to be ingested by the patient for determination of, for example, a carbohydrate bolus dosage determination.

In one embodiment, the testing or monitoring device 140 with a medication dose calculation function may be configured to prompt the patient to select whether to retrieve a predetermined or preprogrammed medication dosage amount such as, for example, a correction bolus or a carbohydrate bolus, following the display of the determined analyte level from the test strip. In this manner, in one embodiment of the present disclosure, the testing or monitoring device 140 with a medication dose calculation function may be configured to automatically prompt the user or patient to select whether a medication dosage determination is desired following an analyte testing using the test strip. Additional information is provided in U.S. patent application Ser. No. 61/149,989 titled "Multi-Function Analyte Test Device and Methods Therefor" filed Feb. 4, 2009, the disclosure of which is hereby incorporated by reference for all purposes in its entirety.

Referring back to FIG. 1, it can be seen that each of the user terminals 120, the financial account terminal 160, and the server terminal 110 are operatively coupled to the data network 130 via a corresponding data communication link 150. Within the scope of the present invention, the data communication link 150 may include wired or wireless communication path which may be configured for secure, encrypted bi-directional data exchange over the data network 130. In particular, the data communication link 150 in one embodiment may include Wi-Fi data communication, IrDA data communication, radio frequency (RF) data communication, infrared data communication, Bluetooth data communication, ZigBee data communication, USB or Firewire cable based data communication, Ethernet cable based data communication, and dial up modem data communication. In other embodiments, the data communication link 150 may include wireless cellular telephone transmission to provide communication over a cellular data network, such as code division multiple access (CDMA) or Global System for Mobile communications (GSM).

For example, in one embodiment, the user terminals 120 may include one of a personal computer (including a desk top or a laptop computer) or a handheld communication device such as a Blackberry™ or iPhone™, Internet access enabled mobile telephones, a bi-directional communication enabled pager, and a communication enabled personal digital assistant (PDA). In one embodiment, the user terminals 120 include an output unit such as a display and/or speakers, an input unit such as a keyboard or a touch-sensitive screen, as well as a controller such as a CPU for performing user instructed procedures at the user terminals 120. Moreover, within the scope of the present invention, the user terminals 120 may be configured to communicate with the data network 130 using a wireless data communication protocol such as Bluetooth, 801.11x, and ZigBee. Additionally, the user terminal 120 may be also configured to communicate with the testing or monitoring device 140 via short range RF communication path, an infrared or IrDA communication path, or using Bluetooth communication protocol. Additionally, the testing or monitoring device 140 may also be configured to connect to the respective user terminals 120 via a wired connection such as a USB connection, an RS-232 cable connection, or an Ethernet cable connection.

Referring again to FIG. 1, the financial account terminal 160 may be configured to communicate with the server terminal 110 and the user terminals 120 over the data network 130 using either or a wired or wireless secure and encrypted connection. As is generally the case, because financial account related information is very sensitive, high level of security for data communication to and from the financial account terminal 130 may be used such as encryption level exceeding 128-key encryption, and the like. Within the scope of the present invention, the financial account terminal 160 may include one of a banking institution terminal, a credit card institution terminal, a brokerage institution terminal, and any other financial institution terminal which maintains a financial account of a user with which financial account transactions may be performed. This aspect of the present invention is discussed in further detail below.

Referring yet again to FIG. 1, the server terminal 110 in one embodiment may include a controller 111 operatively coupled to an input/output (I/O) interface unit 112, a read-only memory (ROM) 113, a random access memory (RAM) 114, and a storage unit 115. In one embodiment, the storage unit 115 includes a server application 116 and an operating system 117. In this manner, the controller 111 may in one embodiment be configured to communicate with the user terminals 120 and the financial account terminal 160 over the data network 110 via the I/O interface unit 112, under the control of the various processes and routines stored in the ROM 113 and the storage unit 115 as well as user transmitted requests and information.

In one embodiment, the server application 116 and the operating system 117 of the storage unit may be configured to provide a proprietary interface for the users, to execute secure and encrypted data communication over the data network 100. More specifically, the server terminal 110 may be configured to provide a proprietary internet-based user interface at a predetermined URL for the users to login from the user terminals 120, for example, for communication with the server terminal 110. Alternatively, within the scope of the present invention, the data network 130 may include the internet, and wherein the server application 116 and the operating system 117 of the server terminal 110 are configured to provide a dedicated website for allowing the users to securely and easily login to their respective accounts using the user terminals 120 over the data network.

Referring still again to FIG. 1, the storage unit 115 of the server terminal 110 in one embodiment may be configured to store data and information related to the user accounts such as, but not limited to, user account login identification and password, user contact information such as telephone and/or facsimile numbers, email address, billing and shipping addresses, user account profile information such as replenishment level information, seasonality or periodicity of user use of the testing or monitoring device, user financial account information (for example, a bank routing number and bank account number in the case of a banking institution), and user testing or monitoring device data information such as the user, strip order history, medication prescription information, such as insulin prescription information, health related monitoring data such as previously measured glucose levels, user specific basal profile information, bolus determination information for medication, e.g., insulin bolus determination information, insulin sensitivity, trend information determined based on the measured glucose levels (and determined by the controller 111), and healthcare provider information for the user such as contact information for the user's physician, hospital, and nursing facilities.

In addition, within the scope of the present invention, the storage unit 115 may further be configured to store an expiration information and or lot number associated with the consumable item, such as a test strip or medication (e.g., insulin), or to calculate expiration information from the lot number. For example, the server terminal 110 may be configured to determine the expiration information of the consumable item prior to or at the time of replenishment transaction (discussed in detail below), based on one or more of several factors, and further configured to transmit the expiration information to the user terminal 120 associated with the replenishment transaction. The one or more of the several factors determining the expiration information associated with the consumable item includes the lot number associated with the consumable item, where each lot number has a unique expiration date associated therewith, a shipment date of the consumable item from the manufacturer, and a date of manufacture of the consumable item.

It will be appreciated by one having skill in the art that a consumable item in reference to analyte monitoring includes any items used in the course of analyte monitoring by the user and the stock of such item must be replenished in order to continue analyte monitoring. In general, consumables include items such as test strips, lancets, and medication, such as insulin. Insulin types may include, but are not limited to, long-acting insulin types such as LANTUS® (insulin glargine), available from Sanofi-Aventis, and LEVEMIR®, available from NovoNordisk, intermediate-acting insulin types such as Neutral Protamine Hagedom (NPH), and LENTE insulin, fast-acting insulin types including recombinant human insulin such as HUMULIN®, available from Eli Lilly and Company, and NOVALIN®, available from NovoNordisk, bovine insulin, and porcine insulin, rapid-acting insulin types such as HUMALOG® (Lysine-Proline insulin), available from Eli Lilly and Company, APIDRA® (glulisine insulin), available from Sanofi-Aventis, and NOVOLOG® (aspart insulin), available from NovoNordisk, and very-rapid-acting insulin types such as VIAJECT™, available from Biodel, Inc.

In this manner, in one embodiment, the user requesting the replenishment transaction for the consumable item will be notified of the expiration information such as the expiration date associated with the consumable item, and will be alerted that the consumable item will not function as optimally beyond the expiration date. In the case of glucose test strips, to ensure the accuracy of the test results showing the measured glucose levels it is important that the user/patient be aware of such expiration date of the glucose test strips, so that the measured glucose levels are as accurate as possible.

Moreover, in the case where there is a physician or treatment advised, such as delivery of medication, including insulin, or other guideline as to frequency of testing or monitoring, such as in Prothrombin Time testing or glucose level testing, a warning signal may be generated and communicated to a healthcare professional or to the user in the case where the consumption of the test materials, as determined by the server terminal 110, is less than the consumption required to meet this frequency of testing or monitoring.

Referring back to the Figure, in one embodiment of the present invention, based on the measured glucose levels for a given patient from a respective user terminal 120, the controller 111 of the server terminal 110 may be configured to determine trend information, including the rate and/or acceleration of analyte level increase or decrease, based on measured glucose levels so as to determine and correspondingly generate for the user terminal 120 for display, a color coded indication of the user's glucose level projections including arrow indicators, color coded warning or notification indicators, and associated audible alerts. For example, based on the user's measured glucose level for a predetermined period of time contemporaneously received from the user terminal 120, the server terminal 110 may be configured to generate and transmit to the user terminal 120 a color coded arrow indicator for display on the user terminal 120 to visually and easily inform the user of the projected or anticipated trend in the glucose level based on the measured glucose levels. In certain embodiments, the display may also indicate patient of conditions such as hypoglycemia, hyperglycemia, impending hypoglycemia, and/or impending hyperglycemia.

Indeed, in one embodiment, an upward directional arrow that is colored red at a steep incline or slope displayed to the user on the user terminal 120 would immediately and readily inform the user that the user's glucose level is rising at a rapid rate and that corrective measures is necessary. On the other hand, a relatively horizontal trend indicator arrow colored in green may inform the user immediately that the user's projected glucose level is at a relatively stable rate and within a predetermined range that is acceptable to the user's profile.

Referring still again to FIG. 1, the server application 116 stored in the storage unit 115 of the server terminal 110 may be configured to perform, under the control of the controller 111, the various procedures and processes as discussed below in conjunction with FIGS. 2-6, as well as to store any information related to the user accounts and profiles within the scope of the present invention.

Figure 2:
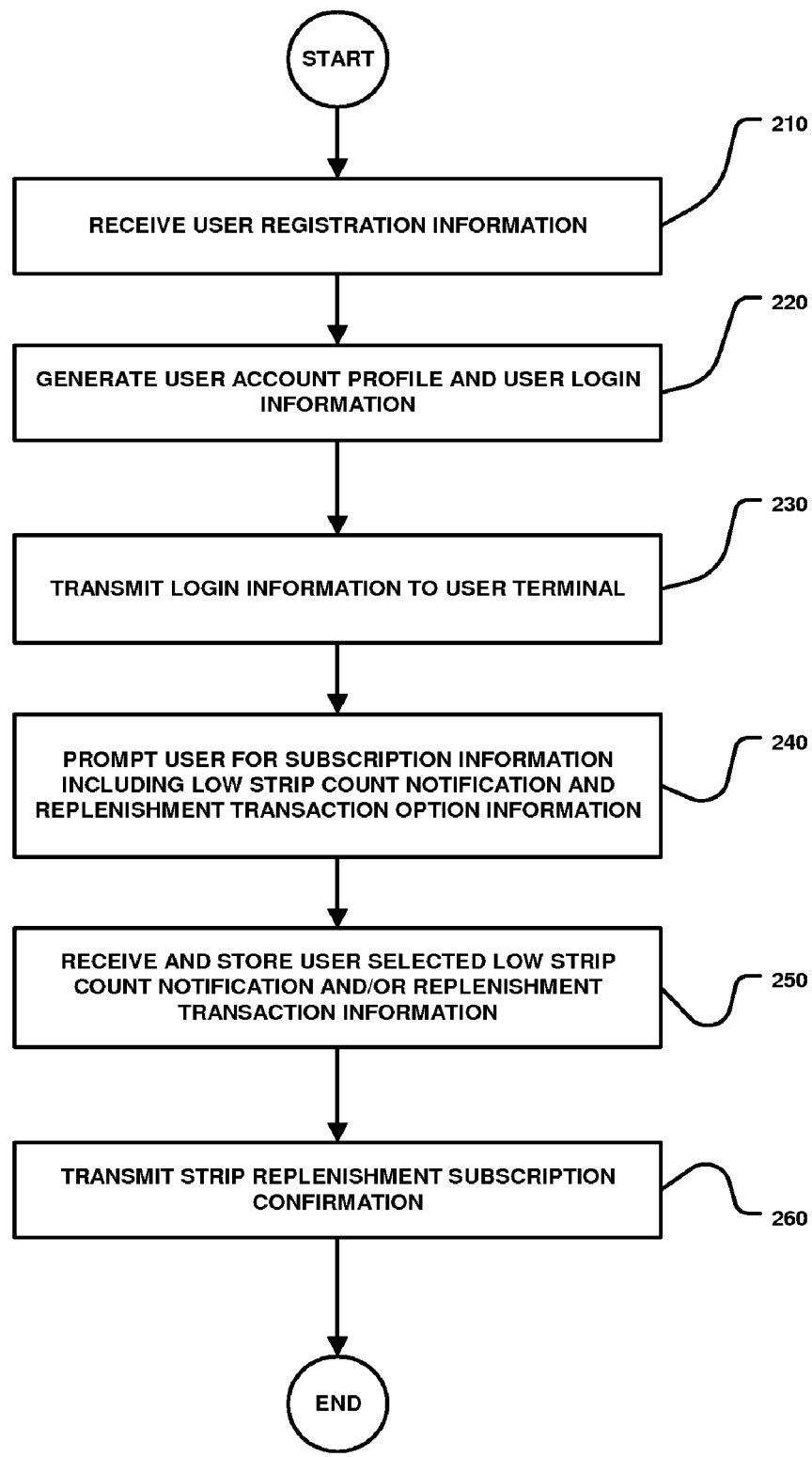
FIG. 2 is a flowchart illustrating user account registration setup and account subscription process in accordance with one embodiment of the present invention.

FIG. 2 is a flowchart illustrating user account registration setup and account subscription process in accordance with one embodiment of the present invention. Referring to the Figure, at step 210, the server terminal 110 (FIG. 1) receives from a user terminal 120 user account registration information. The received user account registration information may include, among others, the user name, user address, the user telephone number, medication prescription information, and the user testing or monitoring device information such as model information of the testing or monitoring device.

Thereafter at step 220, the server terminal 110 is configured to generate a user account profile and login information including password and login identification, all of which are stored in the storage unit 115 of the server terminal 110. Then at step 230, the server terminal 110 is configured to transmit the user login information including the generated login identification information and associated password to the user terminal 120. After transmitting the user login information or alternatively, substantially contemporaneously to the login information transmission, the server terminal 110 is configured to transmit a prompt or request to the user terminal for the user desired subscription information for the consumable replenishment, such as test strip, lancet or medication, such as insulin. In one embodiment, the user desired consumable replenishment subscription information may include the low consumable count threshold notification information and consumable replenishment transaction option information.

More specifically, at step 240, the server terminal 110 in one embodiment is configured to request from the user via the user terminal 120 when the user wishes to be notified of a low consumable, such as strip count, for performing a replenishment procedure, and also, the user's desired purchase transaction option such as establishing a link to the user's financial institution. For example, if the user wishes to be notified of a low consumable, such as strip count level, when the user has, for example, 20 or less strips for usage with the glucose meter, the user may specify 20 as the low strip count level at which point, the user desired notification by the server terminal 110 that replenishment procedure would be necessary. Furthermore, in one embodiment, the replenishment transaction option information provided to the user terminal 120 by the server terminal 110 may include one of establishing a link to the user's financial account institution for processing the purchase transaction for the purchase of the replenishment strips, prompting the user to allow purchase transactions over the data network 130, and a simple replenishment notification with option to perform the purchase transaction for the purchase of the replenishment strips.

Referring again to FIG. 2, at step 250, the server terminal 110 is configured to receive the user selected low consumable, such as strip count, notification and the replenishment transaction information for the user account from the user terminal 120. The server terminal 110 then stores the received information related to the user selected low consumable, such as strip count, notification and the chosen replenishment transaction option in the storage unit 115 associated with the user account information also stored therein.

Then, as can be seen from FIG. 2, the server terminal 110 may be configured to transmit a notification to the user terminal 120 a confirmation of the receipt and the information which the user selected for the low consumable, such as strip count, notification level and the consumable replenishment transaction that the user selected. Thereafter, the user account registration setup and account subscription process shown in FIG. 2 ends.

Figure 3:
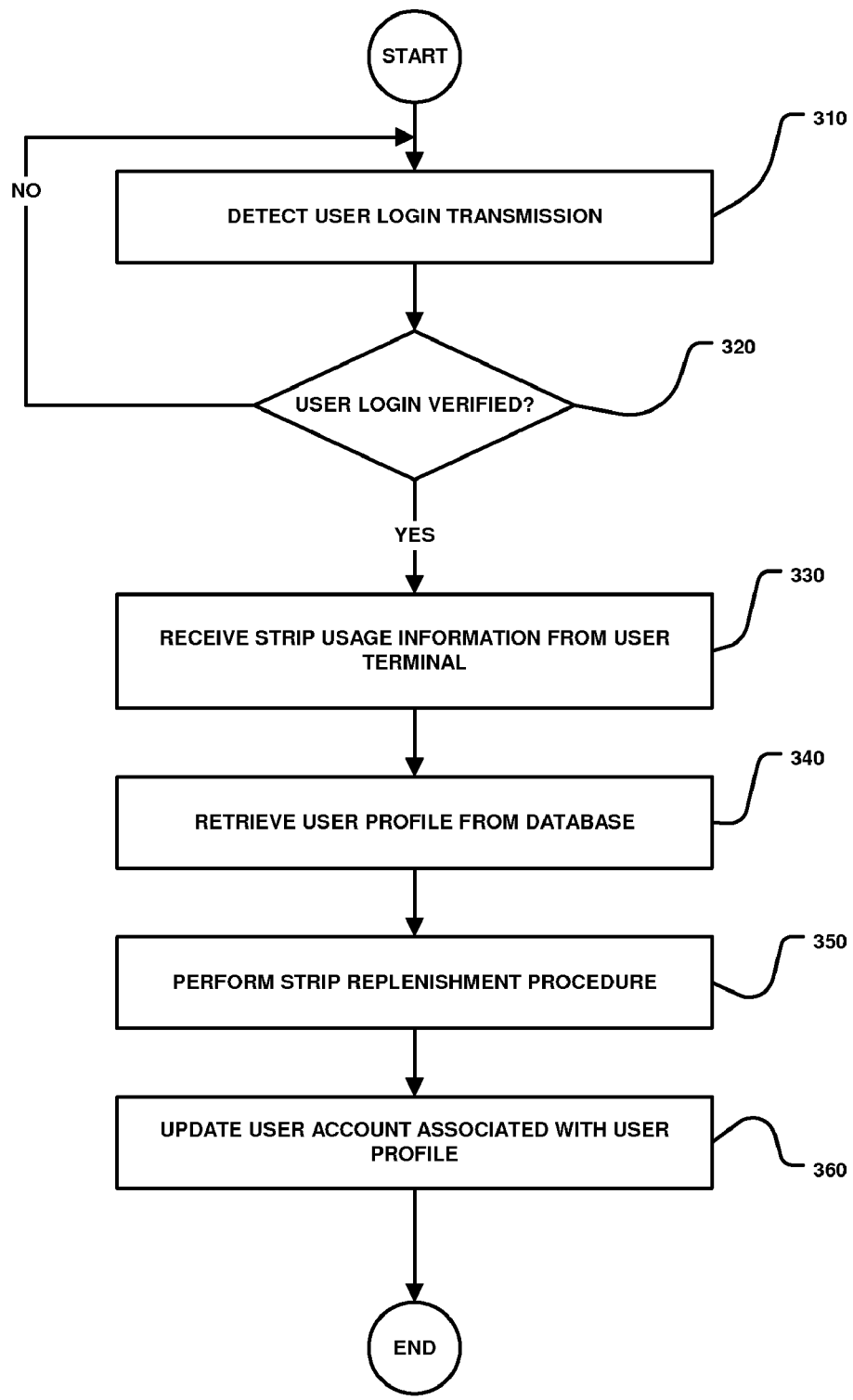
FIG. 3 is a flowchart illustrating an overall replenishment procedure for the user account in accordance with one embodiment of the present invention.

FIG. 3 is a flowchart illustrating an overall replenishment procedure for the user account in accordance with one embodiment of the present invention.

Referring to the Figure at step 310, the server terminal 110 in one embodiment is configured to detect a user login transmission, including, for example, the detection of the user account login identification information and the corresponding password transmitted from the user terminal 120 over the data network 130. Thereafter at step 320, the server terminal 110 is configured to verify the received user account login identification information. That is, in one embodiment, the server terminal 110 is configured to confirm the accuracy of the received account login identification information from the user terminal 120, and to correspond the received account login identification information to a corresponding stored user account. In one embodiment, the server terminal 110 may be configured to search the storage unit 115 (FIG. 1) for a user account profile generated and which corresponds to the received user account login identification information.

Referring to FIG. 3, if at step 320 the received user account login identification information verification fails, the procedure returns to step 310 and awaits for a subsequent transmission of the user account login identification information from the user terminal 120. Optionally, the server terminal 110 may be configured to generate and transmit a login fail notification corresponding to the failed verification of the user account login at step 320 to the corresponding user terminal 120. On the other hand, if at step 320 it is determined that the received user account login identification is verified, and thus, a corresponding user account profile is recognized by the server terminal 110, then at step 330, the server terminal 110 is configured to receive a strip usage information from the user terminal 120 whose user is now logged into the corresponding user account profile.

Thereafter, the server terminal 120 is configured in one embodiment to retrieve the corresponding user account profile from the storage unit 115, for example, (such as in a database associated with the storage of the user account profiles in the storage unit 115). Then, with the strip usage information received from the user terminal 120, and the corresponding user account profile retrieved from the storage unit 115, in one embodiment, the server terminal 110 at step 350 is configured to perform strip replenishment procedure discussed in further detail below to replenish the strip supply associated with the user account profile.

While the present embodiment is described in conjunction with glucose test strips to be used for the periodic glucose level testing, the present invention may be applied and would equally cover any procedure which is configured to replenish a given quantity of consumables (for example, medications, including, for example, insulin, to be consumed at a predetermined time interval). Referring back to the Figure, upon completing the strip replenishment procedure at step 350, the server terminal 110 may be configured to update the user account profile associated with the user by for example, updating the database stored in the storage unit 115 of the server terminal 110 associated with the user account profile for the user that is logged in.

Furthermore, within the scope of the present invention, the database stored in the storage unit 115 may also be linked to systems that are configured to track user demand, so as to forecast and anticipate demand, and also to track overall consumption patterns, preference, seasonal demand, geographic demand, and other similar demographic data for use in managing supply side activities more effectively and efficiently. The individual user data in the database stored in the storage unit 115 may also include insurance or other individual reimbursement coverage rates of the individual user. These data may be used to determine a user co-pay and the amount that the insurance or other individual reimbursement coverage allows to the individual user. The results of these calculation on the user data in the database stored in the storage unit 115 may be used as a basis for purchase or charge transaction to user for the co-pay amount, to charge the insurance or other individual reimbursement coverage for the amount so covered, and also to provide an alert signal in the case that the individual user may exceed the limits of payment coverage, as stored in the database in the storage unit 115, so that action may be taken based on the alert signal.

Figure 4:
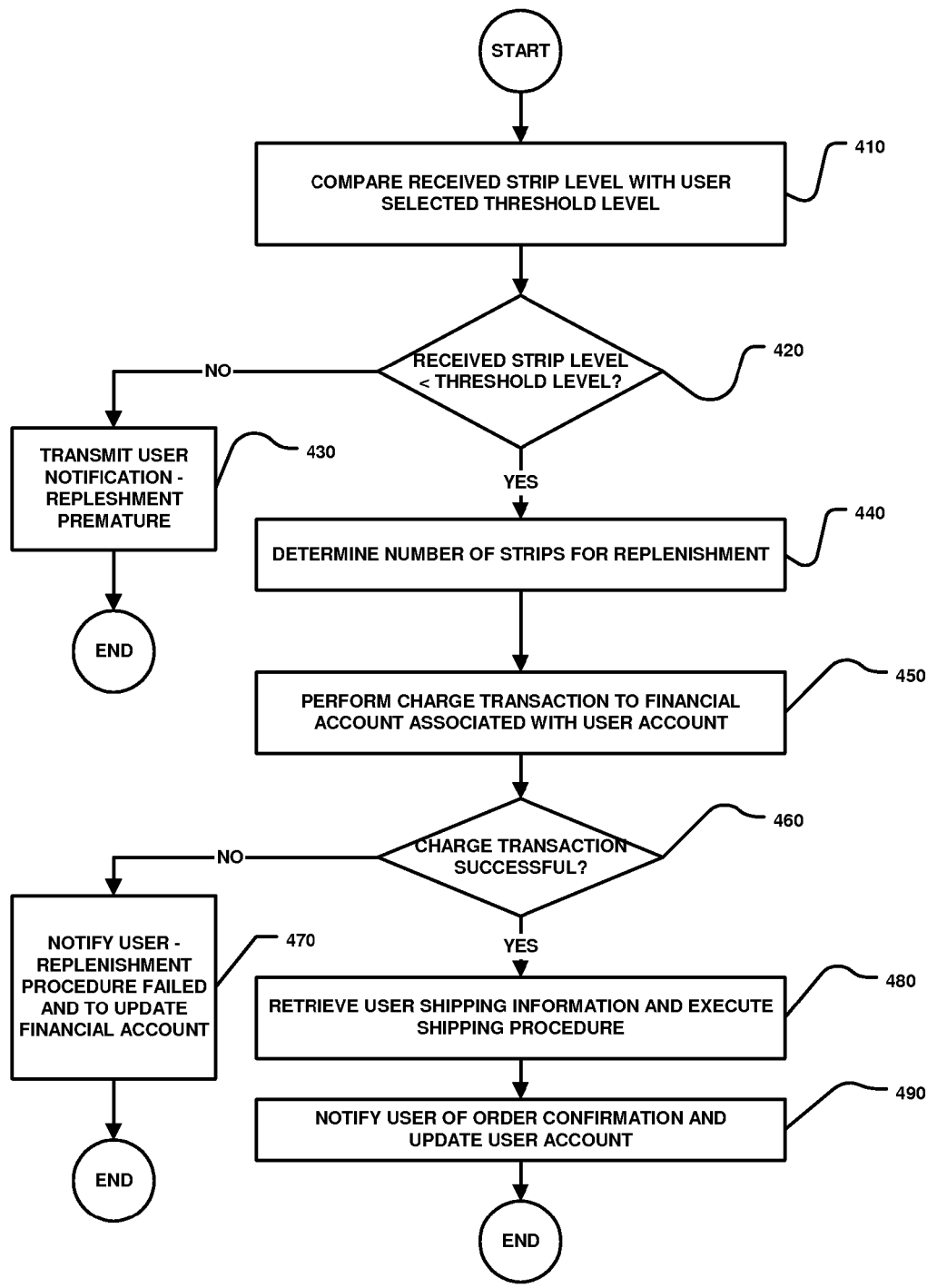
FIG. 4 is a flowchart illustrating the strip replenishment procedure shown in FIG. 3 in further detail in accordance with one embodiment of the present invention.

FIG. 4 is a flowchart illustrating the strip replenishment procedure shown in FIG. 3 in further detail in accordance with one embodiment of the present invention. More specifically, the strip replenishment procedure of step 350 (FIG. 3) in one embodiment begins at step 410 where the server terminal 110 in one embodiment is configured to compare the received strip usage level with a user selected threshold level. Referring back to FIG. 1, the user selected threshold level in one embodiment may correspond to the one or more of low strip count notification level which the user selected during the user account registration procedure as shown in FIG. 2. Moreover, the received strip usage level at step 410 in one embodiment corresponds with the received strip usage information at step 330 (FIG. 3) received from the user terminal 120 (FIG. 1).

Referring back to FIG. 4, after the comparing step at step 410 (or as a result of the comparison step of step 410, the strip replenishment procedure at step 420 determined whether the received strip usage level is below the user selected threshold level. If it is determined at step 420 that the received strip usage level is above the user selected threshold level, then at step 430, the server terminal 110 transmits a user notification to the corresponding user terminal 120 notifying that the replenishment is procedure, and thereafter, the strip replenishment procedure terminates.

On the other hand, if at step 420 it is determined that the received strip usage level is below the user selected threshold level, then at step 440, the server terminal is configured to determine the number of strips that are needed for replenishment. More specifically, the server terminal 110 in one embodiment may be configured to not only determine whether strip replenishment is necessary for the associated user account, but also, what the amount of necessary replenishment should be based on one or more predetermined factors such as the desired or optimal strip level or count selected by the user (and previously stored in the storage unit 115, for example, of the server terminal 110), and the time frame in which the strip replenishment procedure is triggered based upon the user account profile information (that is, based on the user's strip usage history profile, whether the triggered strip replenishment procedure is temporally closer to the most immediately preceding strip replenishment procedure).

Within the scope of the present invention, such usage historical information determined by the server terminal 110, for example, may provide valuable information to the user as well as to the server terminal 110 to maintain an efficient and reliable strip replenishment routine so as to not result in either over supply of strips, or a the supply of strips running dangerously low.

Referring back to FIG. 4, after determining the number of strips that are needed for replenishment at step 440 associated with the user account profile, at step 450, the server terminal 110 in one embodiment is configured to perform a charge transaction to the financial account associated with the user account so as to charge the user's financial account for the purchase and shipping of the replenishment strips to the user associated with the user account profile. In one embodiment, as discussed above, the server terminal 110 is configured to retrieve the financial account information stored and associated with the user account and performs the charge transaction over the data network 130 with the corresponding financial account terminal 150. As discussed above, the financial account information in one embodiment may include one of a bank account, a credit card account a debit account, a pre-paid financial account, or any other cash or cash equivalent account (such as the redemption of airline miles or vendor points) which the server terminal 110 is configured to recognize with monetary value.

Referring again to FIG. 4, at step 460, it is determined whether the charge transaction performed at step 450 is successful. More specifically, the server terminal 110 in one embodiment is configured to interact with the financial account terminal 160 over the data network 130 in order to perform the charge or debit transaction for the amount associated with the number of replenishment strips. If the associated financial account terminal 160 returns a failed transaction notification to the server terminal 110 based on the server terminal 110 transmission of the charge transaction over the data network 130, then at step 470, the server terminal 110 in one embodiment is configured to generate and transmit a notification to the user terminal 120 notifying the user at the user terminal 120 that the strip replenishment procedure has failed. Also, the server terminal 110 is configured to notify the user that the reason for strip replenishment failure is due to inaccurate or outdated financial account information associated with the user account, and thus, is configured to prompt the user to update the user's financial account associated with the user's account profile stored in the server terminal 110.

On the other hand, referring back to FIG. 4, if at step 460, it is determined that the strip replenishment charge transaction is successful, then at step 480, the server terminal 110 is configured to retrieve the user shipping information associated with the user account profile, and executes the shipping procedure to ship the replenishment strips purchased by the user to the user's designated shipping location. In one embodiment, the server terminal 110 may be configured to prompt the user to verify or update the desired shipping location (such as destination address and time frame for shipping to include expedited shipping, for example).

Referring again to FIG. 4, upon executing the shipping procedure at step 480, the server terminal at step 490 is configured to generate and transmit a notification to the user terminal 120 associated with the user account confirming the shipment of the ordered strips as well as the shipping and the fulfilled strip order details. Also, the server terminal 110 is configured to update the associated user account based on the charge transaction and the shipping transaction performed. In this manner, in accordance with one embodiment of the present invention, the users may conveniently place a shipment order of strips in advance of running low on the strips, and rather then relying upon the user's manual calculation or determination of the needed strips based upon the user's strip usage, such determination is automatically performed for the user, and the user can easily make the purchase transactions for the replenishment strips quickly and easily.

Figure 5:
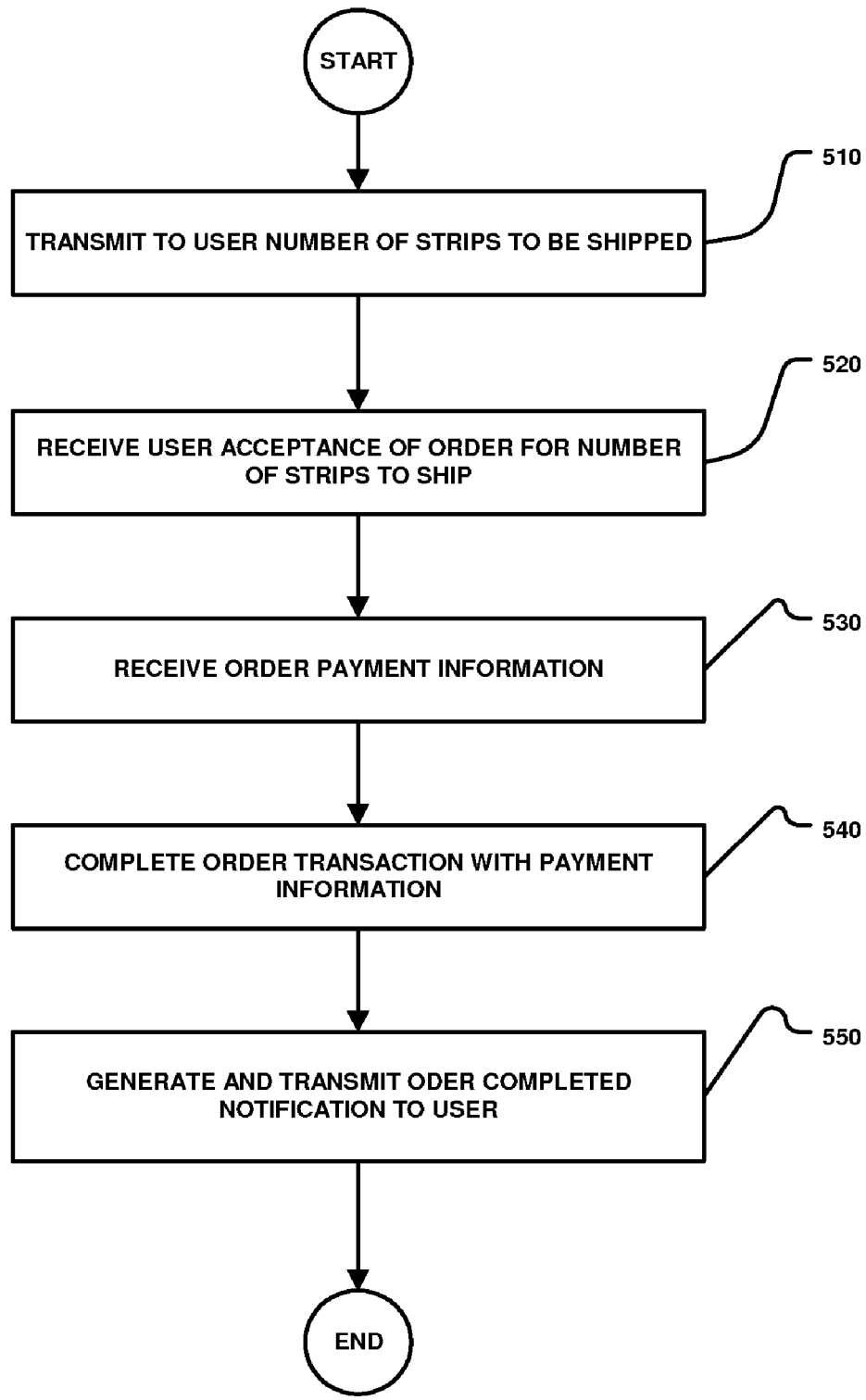
FIG. 5 is a flowchart illustrating the strip replenishment procedure shown in FIG. 3 in further detail in accordance with another embodiment of the present invention.

FIG. 5 is a flowchart illustrating the strip replenishment procedure shown in FIG. 3. in further detail in accordance with another embodiment of the present invention. Referring to the Figure, in one embodiment of the present invention, the server terminal 110 is configured to transmit to the user terminal 120 a predetermined or calculated number of strips to be shipped at step 510. In one embodiment, the server terminal 110 may be configured to determine the number of strips to be shipped based one or more predetermined factors such as the user strip usage level, the user selection of low strip notification information, the user's desired strip inventory, and the user's desired frequency of strip replenishment.

Responsive to the number of strips to be shipped notification received from the server terminal 110, the user may confirm the received number of strips to be shipped as the number of strips that the user wants to receive, and thus, may transmit an acceptance notification to the server terminal 110 which, the server terminal 110 at step 520 is configured to receive, for example, as an acceptance of the order associated with the number of strips to be shipped to the user. Thereafter at step 530, the server terminal 110 may be configured to receive order payment information for the purchase of the number of strips that the user has accepted to be shipped to the user. In one embodiment, the user may transmit from the user terminal 120 to the server terminal 110 over the data network 130, a user financial account information, such as a credit card information or a bank account information to be used to perform the purchase transaction of the strips to the shipped to the user.

Referring back to FIG. 5, thereafter at step 540, the server terminal 110 having received the financial account information from the user terminal 120, performs and completes the order transaction for the purchase of the number of strips accepted by the user and to be shipped to the user with the received payment information. Upon performing and successfully confirming the order transaction at step 540, the server terminal 110 is configured in one embodiment to generate an order confirmation notification and to transmit the notification to the user. In one embodiment, the order confirmation notification may include the number of strips ordered, the shipping or mailing address where the ordered strips are to be shipped, and the amount charged to the financial account associated with the payment information.

In this embodiment, it can be seen that the user is not required to provide the user's financial account information to have it stored, for example, in the user account profile at the server terminal 110. This approach would be particularly desirable for users who do not wish to have their financial account information disseminated and stored in vendor sites such as the server terminal 110 configured to perform strip replenishment procedures.

Figure 6:
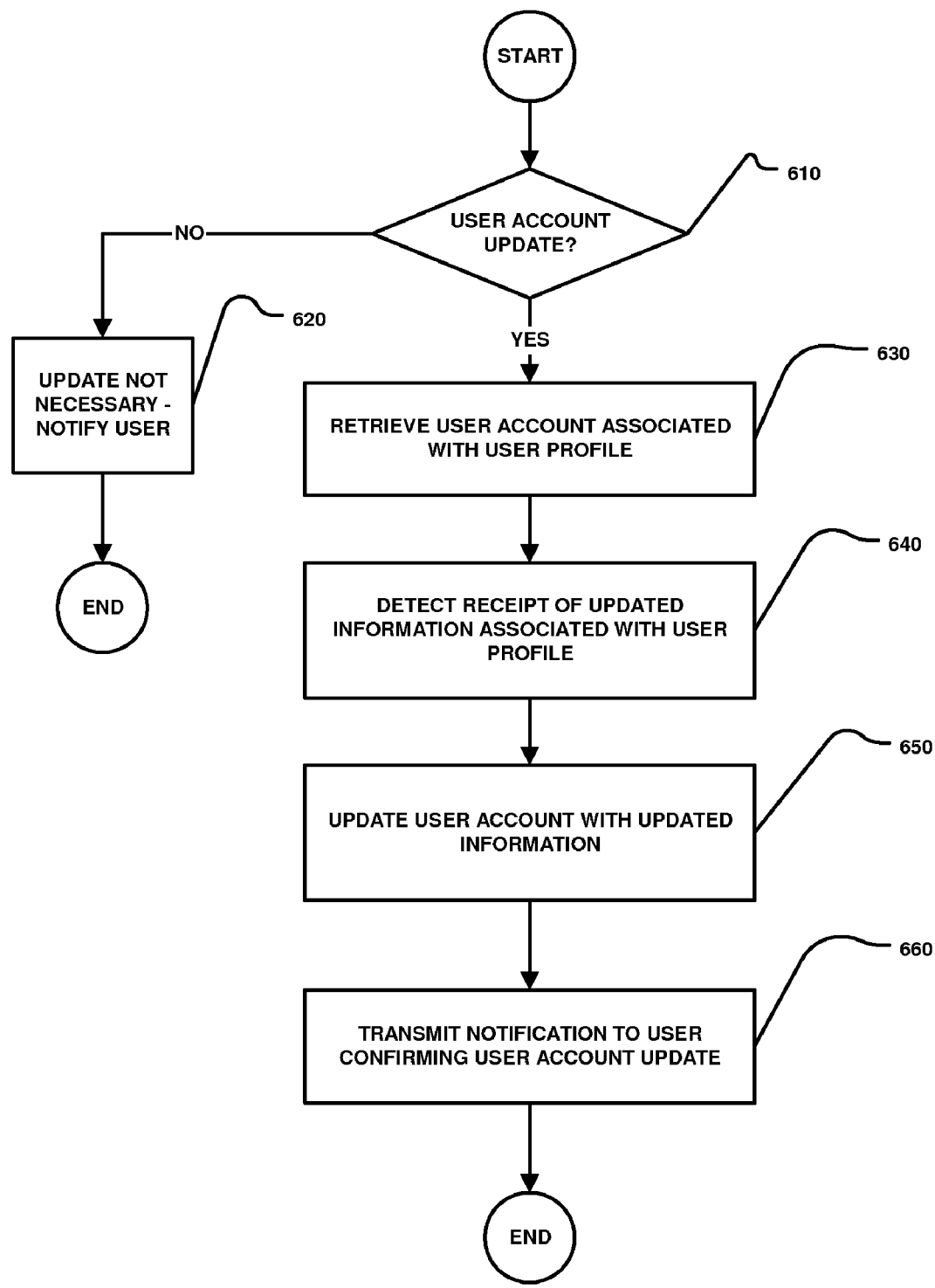
FIG. 6 is a flowchart illustrating a user account update and maintenance procedure in accordance with one embodiment of the present invention

FIG. 6 is a flowchart illustrating a user account update and maintenance procedure in accordance with one embodiment of the present invention. Referring to the Figure, at step 610, a user account update procedure is prompted. This may be a server terminal 110 (FIG. 1) triggered procedure (for example, when it is determined that the user financial account information stored in the server terminal 110 is outdated or no longer accurate), or alternatively, the user at the user terminal 120 may initiate the user account update procedure of step 610 based on the user's desire to modify one or more settings or parameters associated with the user account profile.

Referring to the Figure, in the case where the server terminal 110 determines that the user account update is not needed, then at step 620, it is determined that the account update procedure is unnecessary and a corresponding notification is transmitted to the user terminal 120. For example, in the case where the user prompts a parameter which the user wishes to modify (such as by modifying the shipping information), if the server terminal 110 determines at step 610 that the updated information with which the user wishes to update is the same at that which is stored in the server terminal 110, then, rather then expending the processing power of the server terminal 110 to perform the user account update procedure, the server terminal 110 is configured to generate and transmit the notification to the user terminal that the user specified account is not necessary.

On the other hand, if it is determined that the user account update is to be performed at step 610, then at step 630, the server terminal 110 is configured to retrieve the stored user account associated with the user profile. Thereafter, at step 640, the server terminal 110 is configured to detect the receipt of updated information associated with the user profile received from the user terminal 120. Thereafter, the server terminal 110 at step 650 is configured to update the user account with the updated information received from the user terminal 120. In one embodiment, the server terminal 110 may be configured to update the database stored in the storage unit 115, and which is associated with the user account to be updated based on the account update information received from the user terminal 120. Upon completing the user account update with the received updated information, the server terminal 110 at step 660 is configured to transmit a notification to the user terminal 120 to notify and confirm the update to the user account.

In the manner described above, in accordance with the various embodiments of the present invention, there is provided method and system for providing subscription based transaction for consumable items such as glucose test strips, which diabetic patients may effectively use to easily replenish glucose test strips when the patient is running low on such item. In one embodiment, the user's use of the account or access to the subscription based account profile serves to compare the number of remaining strip counts with the desired minimum number of strips which the patient has specified, and to automatically initiate and execute the purchase transaction of the strips or consumables for the user to order and deliver the strips to the patient on time such that the patient does not run low on the item.

In this manner, in accordance with the various embodiments of the present invention, an efficient system and method for the user to always maintain a minimum number of consumable items on order or to be ordered based on the user's rate of usage of the item are provided.

Furthermore, within the scope of the present invention, the server terminal 110 may be configured to provider a loyalty based rewards program such that based a predetermined criteria, the users may be provided with a discounted price for the replenishment orders of the test strips, and/or be offered a replacement glucose meter for use with the test strip based on the user's replenishment transaction history.

For example, the server terminal 110 may be configured to flag a user account profile which has executed a threshold amount of replenishment transaction (whether based on the number of test strips ordered for replenishment, or based on the total value of the replenishment transactions sum), and to offer an incentive to continue to maintain the user account, and thus with the replenishment transactions. In one embodiment, the server terminal 110 may be configured to automatically offer to send a replacement glucose meter at every calendar year (or at a predetermined frequency) so long as the user's frequency and volume of replenishment transaction satisfies a threshold level. Alternatively, the server terminal 110 may be configured to apply a price discount for future replenishment transactions of test strips based on the user satisfying the threshold level discussed above. In this manner, within the scope of the present invention, the users or patients are provided with an incentive to continue to maintain the user account and to continue performing the replenishment transactions.

Additionally, in a further embodiment of the present invention, where there exists contracts with a provider of insurance or other individual reimbursement, or with a government or authority which provides group discounts when certain conditions are met, such as group price discounts or other special commercial terms, the server terminal 110 may be configured to automatically provide the special commercial terms to the provider of insurance or other individual reimbursement, or to the a government or authority.

The various processes described above including the processes operating in the software application execution environment in the replenishment management system 100 including the server terminal 110, performing the subscription based transaction described in conjunction with FIGS. 2-6, may be embodied as computer programs developed using an object oriented language that allows the modeling of complex systems with modular objects to create abstractions that are representative of real world, physical objects and their interrelationships. The software required to carry out the inventive process, which may be stored in the storage unit of the server terminal 110 in the replenishment management system 100, may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

That which is claimed is:

1. An apparatus, comprising:
a housing;
a port coupled to the housing configured to receive a test strip;
a communication module coupled to the housing;
one or more processors coupled to the housing; and
a memory for storing instructions coupled to the one or more processors which, when executed by the one or more processors, causes the one or more processors to:
generate a signal associated with a detected analyte sample on the test strip received at the port;
determine a frequency of the signal generation associated with the detected analyte sample;
compare the determined frequency to a predetermined threshold level;
generate a consumable replenishment level information based on the comparison;
determine an analyte concentration associated with the detected analyte sample;
retrieve prior administered medication level information including prior stored long acting insulin dose amounts and/or prior stored rapid acting insulin dose amounts, and associated analyte concentration associated with the retrieved prior administered medication level information; and
calculate a current dose level based at least in part on the determined analyte concentration and the retrieved prior administered medication level information such that the calculated current dose level corrects for prior administered medication
wherein the determined current dose level includes a predetermined type of medication classification that includes long acting insulin and/or rapid acting insulin; and
an output unit coupled to the one or more processors and provided in the housing and configured to output one or more data associated with the generated signal and the consumable replenishment level information.

2. The apparatus of claim 1, wherein the signal associated with a detected analyte sample is an analyte concentration.

3. The apparatus of claim 2, wherein the analyte concentration is associated with a blood glucose concentration.

4. The apparatus of claim 3, wherein the display comprises an indicator activatable when the glucose concentration of the sample indicates hyperglycemia.

5. The apparatus of claim 3, wherein the display comprises an indicator activatable when the glucose concentration of the sample indicates hypoglycemia.

6. The apparatus of claim 3, wherein the display comprises an indicator activatable when the glucose concentration of the sample indicates impending hyperglycemia.

7. The apparatus of claim 3, wherein the display comprises an indicator activatable when the glucose concentration of the sample indicates impending hypoglycemia.

8. The apparatus of claim 2, wherein the analyte concentration is associated with a fasting blood glucose concentration.

9. The apparatus of claim 2 wherein the output unit includes one or more of a visual display output, an audible display output, a vibratory display output, or one or more combinations thereof.

10. The apparatus of claim 1, wherein the output unit is further configured to output one or more data associated with the determined frequency, the predetermined threshold level, or the generated replenishment level information.

11. The apparatus of claim 1, wherein the consumable is a test strip, a lancet, or a medication.

12. The apparatus of claim 11, wherein the medication is insulin.

13. The apparatus of claim 12, wherein the insulin is long acting insulin or rapid acting insulin.

14. The apparatus of claim 1, wherein the memory for storing instructions coupled to the one or more processors, which when executed by the one or more processors causes the one or more processors to store one or more of the generated signal associated with the detected analyte sample, the determined frequency of the signal generation, or the generated consumable replenishment level in the memory.

15. The apparatus of claim 1, wherein the communication module is configured to communicate data using a wired communication protocol or wireless communication protocol.

16. The apparatus of claim 15, wherein the wired communication protocol includes one or more of a USB communication protocol, or an RS-232 communication protocol.

17. The apparatus of claim 15, wherein the wireless communication includes one or more of an RF communication protocol, an infrared communication protocol, a Wi-Fi communication protocol, a Zigbee communication protocol, a Bluetooth communication protocol, or cellular telephone transmission.

18. The apparatus of claim 1, wherein the communication module is configured to communicate data using a cellular telephone transmission.

19. The apparatus of claim 1, wherein the communication module is configured to communicate with a terminal server.

20. The apparatus of claim 19, wherein the communication module is configured to retrieve or transmit one or more user information from the terminal server.

21. The apparatus of claim 20, wherein the user information is user account login identification and password, bolus medication determination information, insulin sensitivity, or analyte concentration associated with a detected analyte sample.

22. The apparatus of claim 1, wherein the memory for storing instructions coupled to the one or more processors, which when executed by the one or more processors causes the one or more processors to retrieve one or more medication parameter associated with the generated signal.

23. The apparatus of claim 22, wherein the memory is configured to store the one or more medication parameters.

24. The apparatus of claim 22, wherein the one or more medication parameter includes one or more of a medication classification, a medication type, a medication therapy profile, or a medication usage information.

25. The apparatus of claim 1, wherein the processor is further configured to process the one or more signals produced by the electrochemical sensor in connection with the analyte concentration and determine trending of analyte level.

26. The apparatus of claim 1, wherein said trending provides for a rate and/or acceleration of analyte level increase or decrease.

27. The apparatus of claim 1, wherein the prior administered medication level information is associated with one or more of administered medication dose time information, or administered dose frequency information over a predetermined time period.

28. The apparatus of claim 1, wherein the output unit is configured to output one or more of the determined current dose level, determined analyte concentration, the retrieved prior administered medication level information, the analyte concentration associated with the retrieved prior administered medication level information, or a request for one or more prior stored long acting insulin dose amounts and/or prior stored rapid acting insulin dose amounts.

29. The apparatus of claim 28, wherein the output unit is configured to output a request for an additional analyte sample or a request to confirm the determined current dose level.

30. The apparatus of claim 1 including an input unit coupled to the one or more processors, wherein the memory for storing instructions coupled to the one or more processors which, when executed by the one or more processors causes the one or more processors to detect one or more input commands received from the input unit.

31. The apparatus of claim 30, wherein the one or more input commands includes an acknowledgement confirming the determined current dose level.

32. The apparatus of claim 30, wherein the one or more input commands includes a rejection of the determined current dose level.

33. The apparatus of claim 30, wherein the one or more input commands includes a request to recalculate the current dose level.

34. The apparatus of claim 1, including a communication module operatively coupled to the one or more processors, the communication module configured to transmit one or more of the determined current dose level or the determined analyte concentration to a remote location.

35. An apparatus, comprising:
a housing;
a port coupled to the housing configured to receive a test strip;
a communication module coupled to the housing;
one or more processors coupled to the housing; and
a memory for storing instructions coupled to the one or more processors which, when executed by the one or more processors, causes the one or more processors to:
generate a signal associated with a detected analyte sample on the test strip received at the port;
determine an analyte concentration associated with the detected analyte sample;
retrieve prior administered medication level information including prior stored long acting insulin dose amounts and/or prior stored rapid acting insulin dose amounts, and associated analyte concentration associated with the retrieved prior administered medication level information; and
calculate a current dose level based at least in part on the determined analyte concentration and the retrieved prior administered medication level information such that the calculated current dose level corrects for prior administered medication
wherein the determined current dose level includes a predetermined type of medication classification that includes long acting insulin and/or rapid acting insulin; and
an output unit coupled to the one or more processors and provided in the housing and configured to output one or more data associated with the generated signal.

36. The apparatus of claim 35, wherein the prior administered medication level information is associated with one or more of administered medication dose time information, or administered dose frequency information over a predetermined time period.

37. The apparatus of claim 35, wherein the output unit is configured to output one or more of the determined current dose level, determined analyte concentration, the retrieved prior administered medication level information, the analyte concentration associated with the retrieved prior administered medication level information, or a request for one or more prior stored long acting insulin dose amounts and/or prior stored rapid acting insulin dose amounts.

38. The apparatus of claim 37, wherein the output unit is configured to output a request for an additional analyte sample or a request to confirm the determined current dose level.

39. The apparatus of claim 35 including an input unit coupled to the one or more processors, wherein the memory for storing instructions coupled to the one or more processors which, when executed by the one or more processors causes the one or more processors to detect one or more input commands received from the input unit.

40. The apparatus of claim 39, wherein the one or more input commands includes an acknowledgement confirming the determined current dose level.

41. The apparatus of claim 39, wherein the one or more input commands includes a rejection of the determined current dose level.

42. The apparatus of claim 39, wherein the one or more input commands includes a request to recalculate the current dose level.

43. The apparatus of claim 35, including a communication module operatively coupled to the one or more processors, the communication module configured to transmit one or more of the determined current dose level or the determined analyte concentration to a remote location.

* * * * *

UNITED STATES PATENT AND TRADEMARK OFFICE
CERTIFICATE OF CORRECTION

| | | |
|---|---|---|
| PATENT NO. | : 8,374,925 B2 | Page 1 of 1 |
| APPLICATION NO. | : 12/393891 | |
| DATED | : February 12, 2013 | |
| INVENTOR(S) | : Liamos et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 579 days.

Signed and Sealed this
Eighteenth Day of November, 2014

Michelle K. Lee
*Deputy Director of the United States Patent and Trademark Office*